(12) United States Patent
O'Brien

(10) Patent No.: US 6,333,445 B1
(45) Date of Patent: Dec. 25, 2001

(54) CRYOGENIC SEPARATION PROCESS FOR THE RECOVERY OF COMPONENTS FROM THE PRODUCTS OF A DEHYDROGENATION REACTOR

(75) Inventor: John V. O'Brien, Shrewsbury, MA (US)

(73) Assignee: Chart, Inc., Mayfield Hts., OH (US)

( * ) Notice: Subject to any disclaimer, the term of this patent is extended or adjusted under 35 U.S.C. 154(b) by 0 days.

(21) Appl. No.: 09/446,863

(22) Filed: Dec. 23, 1999

Related U.S. Application Data
(60) Provisional application No. 60/076,543, filed on Mar. 2, 1998, and provisional application No. 60/087,307, filed on May 29, 1998.

(51) Int. Cl.⁷ .................................. C07C 7/00; F25J 3/00
(52) U.S. Cl. .................... 585/809; 585/800; 585/802; 585/655; 62/600; 62/611; 62/613; 62/617; 62/618; 62/619; 62/932; 208/102; 208/103
(58) Field of Search ..................... 585/655, 800, 585/802, 809; 62/600, 611, 613, 617, 618, 619, 932; 208/102, 103

(56) References Cited

U.S. PATENT DOCUMENTS

| | | | |
|---|---|---|---|
| 4,921,514 | * | 5/1990 | Rowles et al. ............................ 62/24 |
| 5,026,952 | * | 6/1991 | Bauer ................................... 585/800 |
| 5,329,774 | * | 7/1994 | Tanguay et al. ......................... 62/23 |
| 5,414,188 | * | 5/1995 | Ha et al. ............................... 585/800 |
| 5,505,048 | * | 4/1996 | Ha et al. ................................ 62/11 |

* cited by examiner

Primary Examiner—Walter D. Griffin
(74) Attorney, Agent, or Firm—Calfee Halter & Griswold, LLP

(57) ABSTRACT

The olefin-hydrogen effluent vapor stream from a dehydrogenation process is separated by a cryogenic separation method utilizing a cryogenic separation system. The method does not require external refrigeration and reheats and portions an expander feed stream to extract energy and controls the warm end and cold end temperature differences in the primary heat exchanger to provide energy savings and economical operation and material use.

25 Claims, 3 Drawing Sheets

CRYOGENIC SEPARATION PROCESS FOR THE RECOVERY OF COMPONENTS FROM THE PRODUCTS OF A DEHYDROGENATION REACTOR

REFERENCE TO PRIOR APPLICATIONS

This application claims the benefit of the filing date of U.S. Provisional Application Serial No. 60/076,543, filed Mar. 2, 1998, and U.S. Provisional Application Serial No. 60/087,307, filed May 29, 1998, and which applications are incorporated herein by reference.

BACKGROUND OF THE INVENTION

The function of a dehydrogenation process, when utilized in hydrocarbon processing, is to convert paraffinic hydrocarbons to their corresponding olefins.

Thus, propane is converted to propylene:

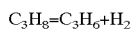
$$C_3H_8 = C_3H_6 + H_2$$

or isobutane is converted to isobutylene:

$$iC_4 = iC_4H_8 + H_2$$

These are two examples of the use of the process.

The reactor effluent stream from such dehydrogenation processes contains these components in the vapor phase. A cryogenic process is employed to condense the $C_3$ or $C_4$ components as a liquid phase product. The residual vapor stream is required free of the $C_3$ or $C_4$ components to minimize their losses.

A method and apparatus for the separation of $C_4$ hydrocarbons from a gaseous mixture containing the same are described in U.S. Pat. Nos. 5,414,188, issued May 9, 1995, and 5,505,048, issued Apr. 9, 1996, hereby incorporated by reference.

These patents are directed to the separation of the $C_4$ hydrocarbons in a series of cooling for condensation, phase separation, and expansion process steps with refrigeration by indirect heat exchange between expansion products to save energy and power consumption.

It is desirable to provide a new and improved cryogenic separation process and apparatus system for the It is desirable to provide a new and improved cryogenic separation process and apparatus system for the separation of $C_3$ or $C_4$ gaseous mixtures with hydrogen, such as produced in dehydrogenation processes to permit the use of lower Cost and more economical materials of construction in the process, to increase the extraction of energy in the process, to reduce the size of heat exchangers employed in the process and apparatus, and to otherwise improve the efficiency and economy of the separation process and apparatus system.

SUMMARY OF THE INVENTION

The invention relates to a cryogenic separation process and system for gaseous, lower hydrocarbon and hydrogen mixtures. In particular, the invention concerns an improved cryogenic separation process and system for the gaseous catalytic reactor effluent of a dehydrogenation process, more particularly, the OLEFLEX™ process (OLEFLEX is a trademark of UOP, Inc. of Des Plaines, Ill., for a dehydrogenation process).

The invention relates to an improved system and process for the separation of $C_3$ or $C_4$ hydrocarbons and hydrogen gaseous mixtures; particularly, those gaseous mixtures which comprise the effluent vapor stream from a catalytic reactor of a dehydrogenation system and process.

The invention comprises a process for the separation of olefinic hydrocarbon in an effluent vapor stream from a paraffinic feed, dehydrogenation reactor and compressed by a compressor, which process comprises partially condensing the olefinic hydrocarbon in the a first warm heat exchanger having a warm end and a cold end; separating the partially condensed olefinic hydrocarbon in a first primary separator to provide a primary vapor product and a first liquid olefinic product; then partially condensing the olefinic hydrocarbon, the primary vapor product in a second cold heat exchanger having a warm end and a cold end to provide a second liquid; then separating the second liquid olefinic hydrocarbon in a second separator to provide a secondary vapor product and a second liquid olefinic product; and isentropically expanding the primary vapor product in a high pressure expander to provide a third liquid olefin stream and a third vapor product. Next, separating the third liquid olefin stream and the third vapor product in a third separator; then reheating the third vapor product in the second cold heat exchanger; dividing the reheated third vapor product into a first portion and a second portion; reheating the first portion in the first warm heat exchanger and withdrawing as the process vapor product essentially hydrogen; isentropically expanding the second fraction in a low pressure expander; reheating the expanded second fraction in the second cold heat exchanger; subcooling a liquid paraffinic feed for use in the reactor in the first warm heat exchanger; combining the subcooled liquid paraffinic feed with the expanded reheated second fraction to provide a combined stream; and totally revaporizing the combined stream in the first warm heat exchanger; then withdrawing the revaporized combined stream and employing the revaporized combined stream as a feed stream to the dehydrogenation reactor.

The process comprises next, combining the first, second, and third liquid olefinic streams to provide a liquid combined stream; rewarming the liquid combined stream to an intermediate temperature between a warm end temperature and a cold end temperature in the first warm heat exchanger; flashing the rewarmed liquid combined stream in a liquid product drum to provide a flashed vapor stream and recycling this vapor stream to a feed compressor; pumping the flashed, rewarmed, liquid combined stream in a pump to a high pressure; reheating the pumped, high pressure, liquid combined stream in the first warm heat exchanger; and withdrawing the reheated, pumped, liquid combined stream from the first warm heat exchanger into a liquid olefin product storage system.

Next, operating the liquid product drum and the pump at a temperature such that the drum, pump, or both may be composed of carbon steel material and operating the expanding of the second fraction in the low pressure expander at a temperature to increase the power output of the expander; and governing the temperature of the cold end of the second cold heat exchanger by the high pressure expander, and the temperature of the warm end of the second cold heat exchanger by the low pressure expander to permit optimization of the size of the first and second heat exchangers.

In a further improvement and embodiment, the process and system comprises an improved cold box for the vapor phase reactor effluent stream, which includes compressing a portion of the compressed effluent vapor stream from the discharge of reactor effluent compressors; cooling the compressed portion of the effluent vapor stream in an aftercooler; separating any condensed liquid from the cooled, compressed, effluent vapor stream and introducing the separated cooled liquid into the product storage drum; partially condensing the remaining compressed effluent vapor stream, which vapor steam is at a higher pressure than the effluent vapor stream in the first warm heat exchanger; and depressurizing the partially condensed, recovering effluent vapor stream and introducing said depressurized, partially condensed, effluent vapor stream into the first primary separator for separation.

The system and process comprises an improved, economical, efficient, cryogenic separation system and a further optional, expander-driven compressor system and process.

The cryogenic separation system and process may be utilized by both propane and isobutune dehydrogenation plants and effluent vapor streams or similar hydrocarbon-hydrogen process streams. The process conditions employed, such as temperature, pressure, and stream compositions are different for propane and isobutane; however, the basic cryogenic separation process and system and their advantages in operation are the same.

The invention will be described for the purposes of illustration only in connection with the preferred embodiment; however, it is recognized that certain changes, modifications and additions may be made to the preferred embodiment, by those skilled in the art, without departing from the spirit and scope of the invention.

DESCRIPTION OF THE EMBODIMENTS

Figure 1:
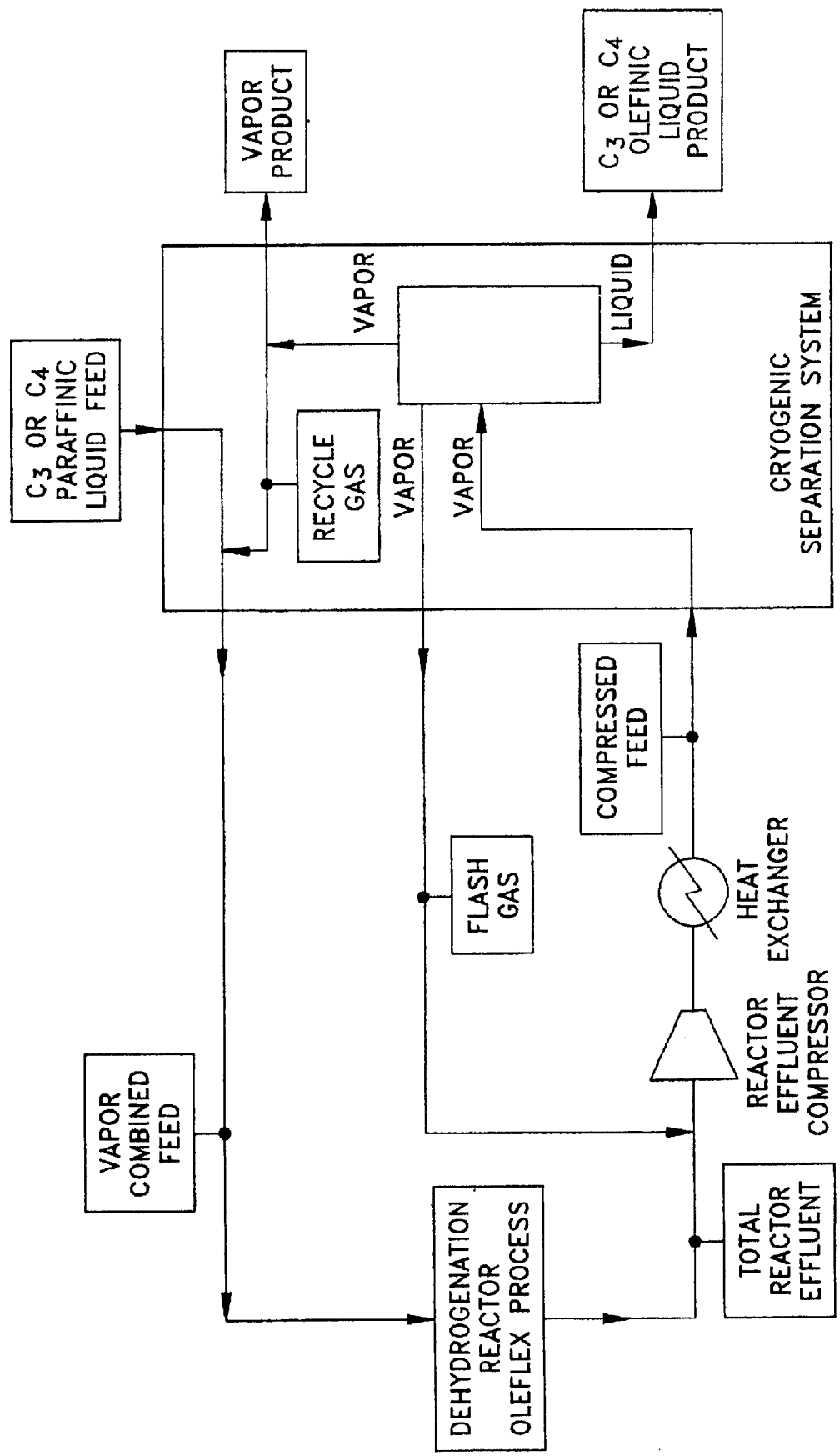
FIG. 1 is a schematic illustration, block flow diagram of the cryogenic separation system of the invention shown as a part on and in an overall dehydrogenation system.

FIG. 1 shows the Cryogenic Separation System (CSS) integrated with an OLEFLEX™ dehydrogenation reactor system and process (OLEFLEX™ is a trademark of UOP Inc. of Des Plaines, Ill.).

The paraffinic hydrocarbon is fed to the CSS as a liquid. In the CSS, it is combined with a recycle gas consisting primarily of hydrogen. This stream is vaporized and emerges as the Combined Feed and is fed to the Oleflex Dehydrogenation Reactor. The Total Reactor Effluent vapor stream contains the olefin components and hydrogen.

This stream is compressed by the Reactor Effluent Compressor, then aftercooled, and is the Compressed Feed to the CSS. A small Flash Gas Stream from the CSS is blended and recycled with this stream to the CSS.

In the CSS, the olefinic components are condensed out of the reactor effluent vapor and recovered as the Liquid Product. The Vapor Product contains the produced hydrogen. A portion of this vapor product stream is the recycle gas in the Combined Feed.

Figure 2:
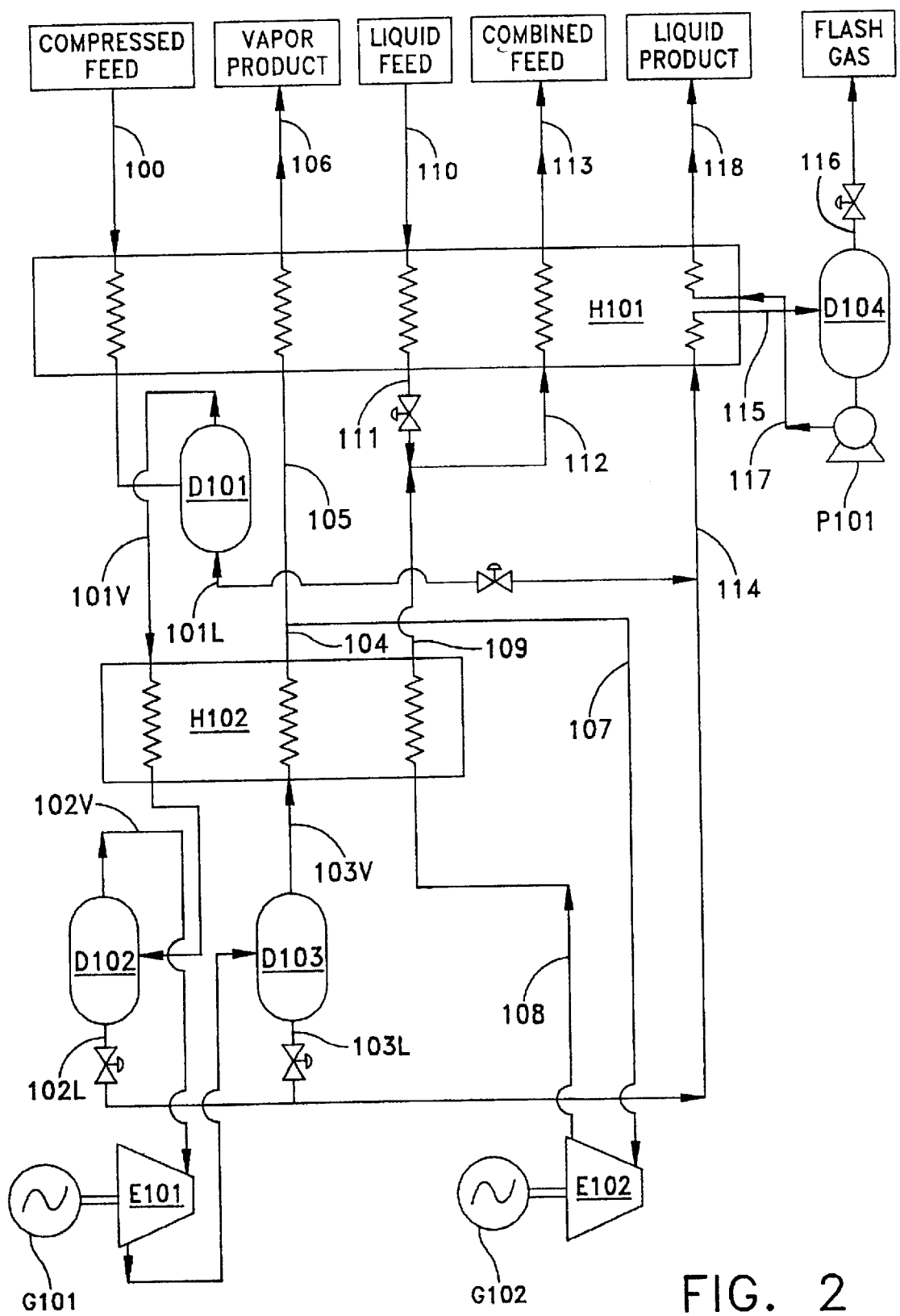
FIG. 2 is a schematic illustration, flow diagram of the cryogenic separation system of FIG. 1.

The Cryogenic Separation System (CSS) of FIG. 2 shows a system design and flow system (with V for vapor and L for liquid) that can be utilized for both propane and isobutane dehydrogenation plants. The process conditions (temperature, pressure, composition) are different from $C_3$ to $C_4$, but the basic process flow scheme is the same.

The process conditions at key points in the cryogenic separation system are listed in the tables below.

The Compressed Feed <100> at near ambient temperature enters the first multipass heat exchanger, the Warm Exchanger, H101. The stream is cooled and partially condensed. The majority, over 95% and typically, over 97% of the propylene or isobutylene is separated out as the liquid stream <101L> in the Primary Separator, D101.

The residual vapor, stream <101V>, then enters the Cold Exchanger, H102. Further olefins are condensed in H102 and are separated as stream <102L> in the Secondary Separator, D102.

The residual vapor, stream <102V>, from D102 is expanded isentropically in the HP (High Pressure) Expander, E101. The outlet expander pressure is set by the Vapor Product pressure required. The liquid in the expander exhaust is separated out in the Tertiary Separator, D103, as stream <103L>.

The Tertiary Separator vapor stream <103V> is reheated in H102 as stream <104>. It is then divided. A portion, stream <105>, is further warmed to ambient temperature in H101 and is exported as the Vapor Product, stream <106>.

The stream, split out from the Vapor Product, is the Recycle Gas, stream <107>. This is expanded isentropically in the LP (Low Pressure) Expander, E102. The inlet expander pressure is set by the Vapor Product pressure. The outlet expander pressure is determined by the Combined Feed Pressure.

The expander exhaust stream is reheated in the Cold Exchanger, H102, as stream <109>. The Liquid Feed <110>, containing the paraffinic components, is subcooled in the Warm Exchanger, H101, to stream <111>. This is combined with the Recycle Gas stream <109> and is a two-phase feed to the Warm Exchanger, H101, stream <112>. This stream is vaporized in H101 and becomes the Combined Feed, stream <113>, to the reactor section.

The liquids from the Primary, Secondary and Tertiary Separators are combined, stream <114>, and reheated in the Warm Exchanger. This stream is withdrawn at an intermediate point along the length of the heat exchanger. It is reheated to a temperature such that the Liquid Product Drum, D104, and Pump, P101, can be of carbon steel materials of construction.

The liquid is pumped to the product storage pressure, then reheated to ambient temperature in H101 and exported as the Liquid Product, stream <118>.

Some vapor is flashed off from the liquid in D104. The temperature and pressure of this drum is controlled, so the vapor pressure of the product liquid is, as required, at the liquid product storage vessel.

The Flash Gas, stream <116>, is recovered by recycling it to the Reactor Effluent Compressor.

The power generated in the HP Expander, E101, is recovered as electric power in the Generator, G101. Similarly, Electric Generator, G102, recovers the power produced in the LP Expander, G102.

| Process Conditions Summary-Propane Dehydrogenation | | |
|---|---|---|
| Stream Compositions | | |
| | Mole %, Range | |
| Compressed - Vapor Feed | | |
| $H_2$ | 35–50 | |
| $CH_4 + C_2H_6$ | 1–5 | |
| $C_3H_8 + C_3H_6$ | 40–60 | |
| $C_4+$ | 0–1 | |
| Liquid Product | | |
| $H_2 + CH_4 + C_2$'s | 1–6 | |
| $C_3H_8 + C_3H_6$ | 94–99 | |
| $C_4+$ | 0–1 | |
| Vapor Product | | |
| $H_2$ | 88–96 | |
| $C_1+$ | 12–4 | |
| Stream Temperatures and Pressures | | |
| Stream Number in | Ranges | |
| FIG. 2 | Temperature, °C. | Pressure, kPag |
| 100 | +40 to +50 | 900 to 1200 |
| 101V | −70 to −90 | 900 to 1200 |
| 102V | −100 to −120 | 900 to 1200 |
| 103V | −120 to −140 | 500 to 800 |
| 107 | −75 to −95 | 500 to 800 |
| 115 | −40 to 0 | 300 to 600 |
| 112 | −75 to −95 | 50 to 400 |
| 118 | +35 to +47 | 3500 to 4000 |

Liquid Product Recovery $$\frac{(C_3H_8 + C_3H_6) \text{ in liquid product}}{(C_3H_8 + C_3H_6) \text{ in compressed vapor feed}} = 99.4 \text{ to } 99.8\%$$

| Process Conditions Summary-Isobutane Dehydrogenation | | |
|---|---|---|
| Stream Compositions | | |
| | Mole %, Range | |
| Compressed - Vapor Feed | | |
| $H_2$ | 40–50 | |
| $CH_4 + C_2$'s + $C_3$'s | 2–8 | |
| $iC_4H_{10} + iC_4H_8$ | 40–60 | |
| Liquid Product | | |
| $H_2 + C_1 + C_2$'s + $C_3$'s | 1–6 | |
| $iC_4H_{10} + iC_4H_8$ | 90–99 | |
| Vapor Product | | |
| $H_2$ | 88–96 | |
| $C_1+$ | 12–4 | |
| Stream Temperatures and Pressures | | |
| Stream Number in | Ranges | |
| FIG. 2 | Temperature, °C. | Pressure, kPag |
| 100 | +40 to +50 | 800 to 1200 |
| 101V | −30 to −60 | 800 to 1200 |
| 102V | −70 to −100 | 800 to 1200 |
| 103V | −100 to −120 | 800 to 1200 |
| 107 | −35 to −65 | 400 to 600 |
| 115 | −40 to 0 | 5 to 100 |
| 112 | −35 to −65 | 50 to 300 |
| 118 | +35 to +47 | 2500 to 3500 |

Liquid Product Recovery $$\frac{(iC_4H_{10} + iC_4H_8) \text{ in liquid product}}{(iC_4H_{10} + iC_4H_8) \text{ in compressed vapor feed}} = 99.0 \text{ to } 99.5\%$$

In the described process scheme of FIGS. 1 and 2, the overall process refrigeration is provided by:
1. The pressure difference between the Compressed Feed and the Vapor Product, e.g., typically 200 to 500 kPa.
2. The pressure difference between the Vapor Product and the Combined Feed, e.g., typically 200 to 400 kPa.
3. The phase change from liquid to vapor for the Liquid Feed.
4. The power extracted by the HP and LP Expanders.

No external refrigeration is required, either as a single cycle propane or propylene system, or, particularly, as a cascade refrigeration system, requiring an additional ethylene cycle.

The novel aspects of this system and process, in combination, provide important economical advantages. The liquid product drum and pump are at a temperature, e.g., warmer than −45° C., such that they can be constructed from carbon steel materials; the liquid product drum and pump are positioned in the process and system such that the heat input from the pumping energy requirement and its resultant fluid temperature rise, e.g., less than 2 to 3° C., have minimal impact on process cycle efficiency; in prior art, this drum and pump are located at cold temperature, on stream <114>, at between −80° C. and −120° C., where they have to be of stainless steel materials; furthermore, at this location, the temperature rise on the pump directly raises the cold liquid inlet temperature into H101 by up to 3° C.; this impacts the cold end temperature difference between the warm and cold streams in the warm heat exchanger, H101, and considerably increases the heat transfer area and size requirement for H101. The position of the LP Expander in the process design is also important, by reheating the expander feed, stream <107>, the energy extracted by the turbine E102 is increased; and the temperature of stream <107>, and hence D101, can be optimized, so the sizes (surface area) of heat exchangers H101 and H102 are minimized and costs reduced; and the expander E101 controls the cold end temperature approach of cold heat exchanger, H102, while expander E102 governs the warm end temperature approach.

Thus, these design features result in a highly economic design for the total separation system.

Figure 3:
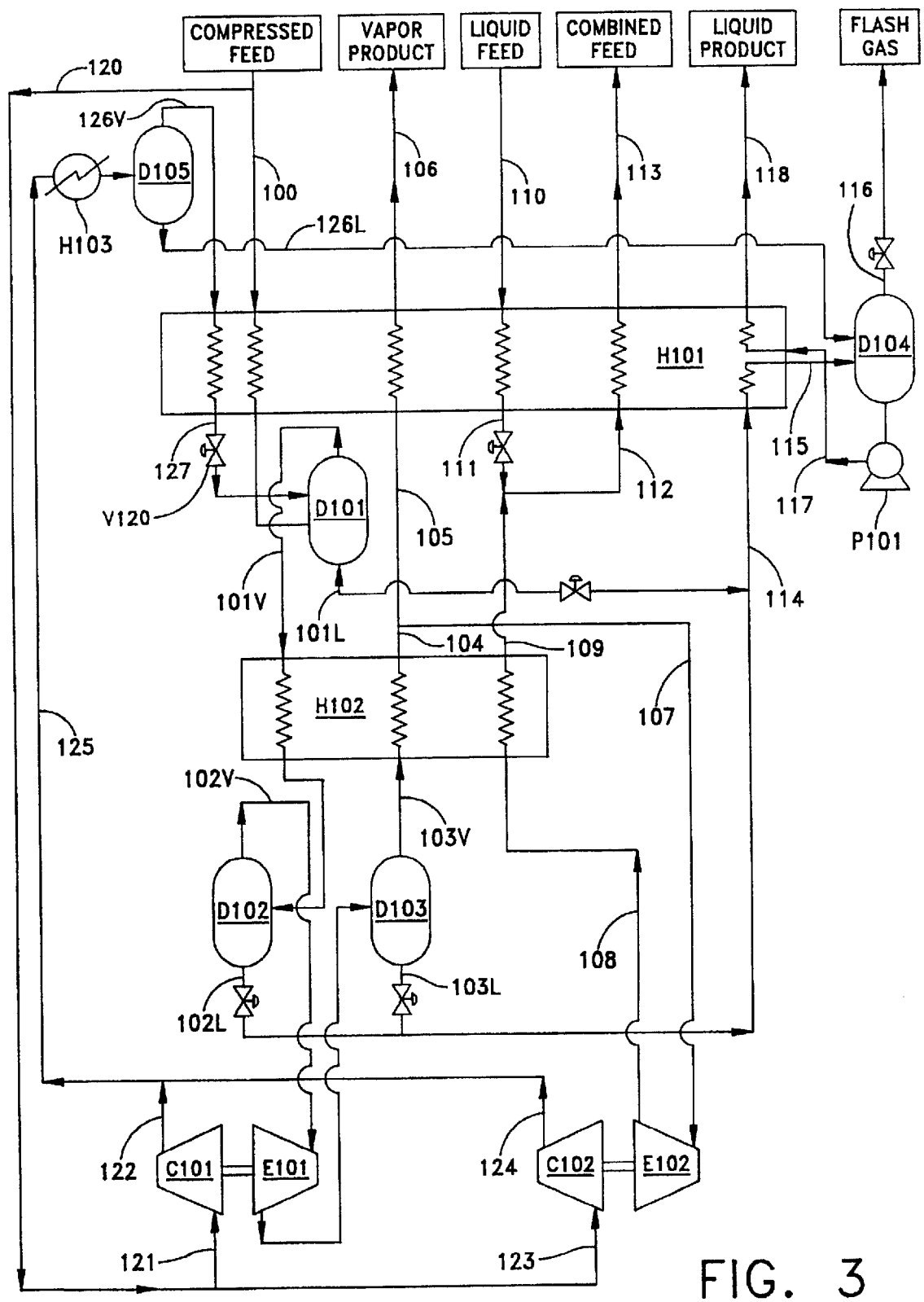
FIG. 3 is a schematic illustration, flow diagram of the cryogenic separation system of FIGS. 1 and 2, but showing the optional use of an expander-driven compressor system.

A further embodiment shown in FIG. 3 is the use of each of the expander power outputs to drive directly a single wheel centrifugal compressor, rather than an electric generator set. This option has a significant impact on the cost of the separation system.

The difficulty of using compressors directly driven by expanders is in finding a suitable stream on which to locate the compressors). The vapor product stream, for instance, has a low molecular weight, about 4, being over 90% $H_2$. This low molecular weight results in stream pressure increase and suction volume flow that does not permit direct coupling of a single wheel compressor with the expander.

FIG. 3 shows a design and process of an adequately high molecular weight stream to the compressors. The Compressed Feed, stream <100>, has between 10 and 25% split off, in stream <120>.

Each expander drives a compressor, C101 and C102. This stream flows through each compressor, shown operating in parallel (or in series). The outlet streams <122> and <124> are combined as stream <125>. This stream is at significantly higher pressure (by 5 to 10 bar) than the Combined Feed. After flowing through the Aftercooler, H103, any liquids condensed out are separated in Drum D105 as stream <126L>. These liquids join the Liquid Product in Drum D104.

The vapor, stream <126V>, is partially condensed in the Warm Exchanger, H101. This stream is depressurized cross a control valve, V120, and fed to the Primary Separator, D101.

The novel aspects of this system and process design, in combination, are:

1. The expander driven compressors are fed with a stream having a molecular weight such that a single wheel, direct driven compressor can be used. These compressors can be run it parallel, as shown, or in series. The electric generators are eliminated, together with their switching gear and the requirement to operate the expanders at constant speed. There is a considerable cost savings with this approach. Furthermore, the ability to vary the expander/compressor speed improves the plant flexibility and efficiency.

2. The portion of the combined feed at a higher pressure increases the temperature approach between the hot and cold streams in the Warm Exchanger, H101 and permits and reduces the size of the warm heat exchanger.

3. Alternatively, the compressed vapor feed pressure can be reduced to achieve the same size for warm heat exchanger, H101, which reduces the discharge pressure and power consumption of the Reactor Effluent Compressor.

What is claimed is:

1. A process for the separation of an olefinic hydrocarbon and hydrogen in a compressed effluent vapor stream from a dehydrogenation reactor, which process comprises:
   a) partially condensing the compressed effluent vapor stream in a first warm heat exchanger having a warm end and a cold end;
   b) separating the partially condensed compressed effluent vapor stream in a first primary separator to provide a first vapor product and a first liquid olefinic product;
   c) partially condensing the first vapor product in a second cold heat exchanger having a warm end and a cold end;
   d) separating the partially condensed first vapor product in a second separator to provide a second vapor product and a second liquid olefinic product;
   e) isentropically expanding, in a high pressure expander, the second vapor product to provide a third liquid olefin product and a third vapor product;
   f) reheating the third vapor product in the second cold heat exchanger;
   g) dividing the reheated third vapor product into a first portion and a second portion;
   h) reheating the first portion in the first warm heat exchanger and withdrawing a process vapor product comprising essentially hydrogen;
   i) expanding the second portion in a low pressure expander;
   j) reheating the expanded second portion in the second cold heat exchanger;
   k) subcooling a liquid paraffinic feed for use in the reactor in the first warm heat exchanger;
   l) combining the subcooled liquid paraffinic feed with the expanded reheated second portion to provide a combined stream;
   m) revaporizing the combined stream in the first warm heat exchanger;
   n) withdrawing the revaporized combined stream;
   o) combining the first, second, and third liquid olefinic products to provide a liquid combined stream;
   p) rewarming the liquid combined stream to an intermediate temperature between a warm end temperature and a cold end temperature in the first warm heat exchanger;
   q) flashing the rewarmed liquid combined stream in a liquid product drum to provide flashed vapor stream;
   r) pumping the flashed, rewarmed, liquid combined stream to a high pressure;
   s) reheating the pumped, high pressure, liquid combined stream in the first warm heat exchanger; and
   t) withdrawing the reheated, pumped, liquid combined stream from the first warm heat exchanger.

2. The process of claim 1 wherein the effluent vapor steam comprises either a $C_3$ or a $C_4$ olefin and hydrogen.

3. The process of claim 1 wherein the paraffinic feed comprise either propane or isobutane.

4. The process of claim 1 which includes carrying out the process without the employment of external refrigeration.

5. The process of claim 1 which includes driving one or more electric generators by the power produced in the high pressure expander, low pressure expander, or both expanders.

6. The process of claim 1 which includes driving one or more centrifugal compressors by the power produced in the high pressure expander, low pressure expander, or both expanders.

7. The process of claim 6 which includes:
   a) splitting a compressed effluent sidestream from the compressed effluent vapor stream;
   b) compressing the compressed effluent sidestream by the driven centifugal compressor;
   c) cooling the compressed effluent sidestream in an aftercooler;
   d) separating condensed liquid from the cooled compressed effluent sidestream and introducing the separated condensed liquid into a product storage drum;
   e) partially condensing the remaining cooled compressed effluent sidestream in the first warm heat exchanger; and
   f) depressurizing the partially condensed effluent sidestream and introducing said depressurized partially condensed effluent sidestream into the first primary separator for separation.

8. The process of claim 7 wherein the compressed portion of the compressed effluent vapor stream, by the centrifugal compressor, comprises from about 10 to 25 percent of the compressed effluent vapor stream.

9. The process of claim 1 which includes employing as the paraffinic hydrocarbon feed stream to the dehydrogenation reactor, a propane or isobutene feed stream.

10. A separation system which utilizes the process of claim 1 for separating an olefinic hydrocarbon and hydrogen in a compressed effluent vapor stream from a dehydrogenation reactor comprising:
   a) a first warm heat exchanger having a warm end and a cold end for partially condensing the compressed effluent vapor stream, reheating a first portion of a reheated third vapor product, vaporizing a combined stream of a subcooled liquid parafin feed and an expanded reheated second portion of the reheated third vapor product, warming a combined stream of first, second, and third liquid olefinic products, and reheating a high pressure liquid combined stream;

b) a first primary separator in which the partially condensed compressed effluent vapor stream is separated to provide a first vapor product and the first liquid olefinic product;

c) a second cold heat exchanger having a warm end and a cold end for partially condensing the first vapor product, reheating a third vapor product and reheating an expanded portion of the third vapor product;

d) a second separator in which the partially condensed first vapor product is separated to provide a second vapor product and the second liquid olefinic product;

e) a high pressure expander for isentropically expanding the second vapor product to provide the third liquid olefin product and the third vapor product;

f) a third separator in which the reheated third vapor product is divided into a first portion and a second portion;

g) a low pressure expander for expanding the second portion of the third vapor product;

h) a liquid product drum for flashing the rewarmed liquid combined stream to provide a flashed vapor stream.

11. The process of claim 1 which includes maintaining the warm end of the first warm heat exchanger at a temperature of about +40 to +50° C.

12. The process of claim 1 which includes maintaining the cold end of the first warm heat exchanger at a temperature of about −30 to −90° C.

13. The process of claim 1 which includes rewarming the liquid combined stream at an intermediate temperature of about −30 to −95° C.

14. The process of claim 1 wherein the second portion comprises from about 25% to 50% by volume of the reheated third vapor product.

15. The process of claim 1 which includes pumping the liquid combined stream to a high pressure of about 2500 to 4000 kPa.

16. The process of claim 1 which includes employing the withdrawn revaporized combined stream as a feed stream to a dehydrogenation reactor.

17. The process of claim 1 which includes introducing the withdrawn reheated, pumped liquid combined stream into a product storage system.

18. The process of claim 1 which includes expanding the second vapor portion in a low pressure expander at a temperature to increase the power output of the expander.

19. The process of claim 1 which includes governing the temperature of the cold end of the second cold heat exchanger, and the temperature of the warm end of the second cold heat exchanger, to permit optimization of the size of the first and second heat exchangers.

20. The process of claim 1 which includes maintaining the liquid product drum and pump at a temperature warmer than −45° C.

21. The process of claim 1 which includes separating the third liquid olefin product and the third vapor product in a third separator.

22. The process of claim 1 which includes isentropically expanding the second portion in a low pressure expander.

23. The process of claim 1 which includes recycling the flashed vapor stream to a feed compressor.

24. The process of claim 1 which includes maintaining the liquid product drum or pump at a temperature such that the drum or pump or both may be composed of carbon steel.

25. The process of claim 1 which includes driving direct single wheel compression by power produced in the high pressure expander, low pressure expander or both expanders.

* * * * *